(12) United States Patent
Minakawa

(10) Patent No.: US 9,046,517 B2
(45) Date of Patent: Jun. 2, 2015

(54) CYSTATIN C ADSORPTION INHIBITOR

(75) Inventor: Yasunori Minakawa, Gosen (JP)

(73) Assignee: DENKA SEIKEN CO., LTD., Tokyo (JP)

( * ) Notice: Subject to any disclaimer, the term of this patent is extended or adjusted under 35 U.S.C. 154(b) by 895 days.

(21) Appl. No.: 13/060,215

(22) PCT Filed: Aug. 24, 2009

(86) PCT No.: PCT/JP2009/064729
§ 371 (c)(1),
(2), (4) Date: Feb. 22, 2011

(87) PCT Pub. No.: WO2010/021399
PCT Pub. Date: Feb. 25, 2010

(65) Prior Publication Data
US 2011/0143457 A1 Jun. 16, 2011

(30) Foreign Application Priority Data
Aug. 22, 2008 (JP) ................... 2008-214513

(51) Int. Cl.
G01N 31/00 (2006.01)
C12M 3/00 (2006.01)
G01N 33/543 (2006.01)

(52) U.S. Cl.
CPC .. G01N 33/54393 (2013.01); *G01N 2333/8139* (2013.01)

(58) Field of Classification Search
CPC .......... A61K 38/00; A61K 39/00; B01L 9/00; C07K 5/00; C07K 14/705; C07K 16/18; G01N 33/582; G01N 33/6893
See application file for complete search history.

(56) References Cited

U.S. PATENT DOCUMENTS

| 8,420,613 B2 * | 4/2013 | Gan et al. ............... 514/44 A |
| 8,524,452 B2 * | 9/2013 | Minakawa et al. ......... 435/7.1 |
| 2004/0185572 A1 | 9/2004 | Kakuta et al. |

FOREIGN PATENT DOCUMENTS

| EP | 1 498 732 A2 * | 3/2005 | ........... G01N 33/543 |
| EP | 2 299 271 A1 | 3/2011 | |
| JP | 6-66798 A | 3/1994 | |
| JP | 9-68529 A | 3/1997 | |
| JP | 10-332697 A | 12/1998 | |
| JP | 11-64333 A | 3/1999 | |
| JP | 2000-193662 A | 7/2000 | |
| JP | 3-342819 B2 | 11/2002 | |
| JP | 3-398372 B1 | 4/2003 | |
| JP | 2003-149244 A | 5/2003 | |
| JP | 2003-177125 A | 6/2003 | |
| JP | 2004-271226 A | 9/2004 | |
| WO | WO 02/086492 A1 | 10/2002 | |

OTHER PUBLICATIONS

Tanaka et al. (Clinical Biochemistry, 2004, vol. 37, pp. 27-35).*
Extended European Search Report issued Jan. 5, 2012, in European Patent Application No. 09808334.8.
Tanaka at al., "A sol particle homogenous immunoassay for measuring serum cystatin C," Clinical Biochemistry (2004). vol. 37, pp. 27-35.
Adachi, The present status and future role of a reagent for measuring serum Cystatin C based on colloidal gold assay, Seibutsu Shiryo Bunseki, 2007, vol. 30, No. 3, pp. 228-232, III. 2. (with English abstract).
Nakayama et al., "Micro-quantity protein/peptide handline for proteomics," Chromatography, 2001, vol. 22, pp. 95-96, Ketsuron (with English abstract).
Rebeski et al., "Identification of unacceptable background caused by non-specific protein adsorption to the plastic surface of 96-well immunoassay plates using a standardized enzyme-linked immunosorbent assay procedure," J. Immunol. Methods, 1999, vol. 226, pp. 85-92.
Saito, K., Summary of "The 13th Annual Meeting of the Society of Analytical Bio-Science; Measurement of Cystatin C and its Significance in Clinical Studies," [online], Mar. 14, 2003, [searched on Feb. 8, 2008], Internet <URL: http://www.higo.ne.jp/anal-bio-sci13/NewFiles/saitou.html>.
Xu et al., "Separation Analysis using Microchip Technology," Chromatography, 2001, vol. 22, p. 7-8 (with English abstract).

* cited by examiner

*Primary Examiner* — Lisa Cook
(74) *Attorney, Agent, or Firm* — Birch, Stewart, Kolasch & Birch, LLP

(57) ABSTRACT

Disclosed is a method by which the adsorption of cystatin C to a container can be inhibited in a simple manner to improve the accuracy of the measurement of cystatin C. Provided are: a cystatin C adsorption inhibitor comprising a non-ionic surfactant; a cystatin C measurement reagent comprising the adsorption inhibitor; and a cystatin C measurement kit. Also provided is a method of inhibiting the adsorption of cystatin C, the method comprising bringing a cystatin C-containing sample into contact with a measurement instrument in the presence of a non-ionic surfactant. The aforementioned non-ionic surfactant is preferably a polyoxyethylene-type surfactant. Alternatively, the aforementioned non-ionic surfactant has preferably a phenoxy structure, more preferably a benzylphenoxy structure.

5 Claims, No Drawings

CYSTATIN C ADSORPTION INHIBITOR

TECHNICAL FIELD

The present invention relates to a cystatin C adsorption inhibitor and a method of inhibiting the adsorption of cystatin C.

BACKGROUND ART

Cystatin C is produced as cysteine protease by nucleated cells throughout the body. Cystatin C belongs to the cystatin superfamily and is a basic low-molecular-weight protein having a molecular weight of 13 kD. In clinical tests, it has been drawing attention as a marker of renal function to replace creatinine (see Non-patent Document 1). In clinical tests, since a large number of specimens are handled at once, an automated accurate means for quantifying cystatin C is required.

As a method of quantifying cystatin C, for example, a latex turbidimetric assay in which latex bound to an anti-human cystatin C antibody is used to measure the absorption or scattering of visible light (see Patent Document 1) and an enzyme labeling method (see Patent Document 2) are known.

There is also known a method of examining a renal disease, which method is characterized by measuring the concentration of cystatin C excreted into urine and the concentration of an endogenous clearance substance, creatinine, to calculate the ratio of the cystatin C concentration and the creatinine concentration and using the thus obtained data (see Patent Document 3).

Patent Document 4 describes a method of quantifying cystatin C in which a prozone phenomenon inhibitor for measurement of immunological reactions is employed, the inhibitor being characterized by comprising one or more sulfate ester-based and sulfonate-based anionic surfactants.

It has been indicated that cystatin C, because of its physical properties, is likely to adsorb to plastic and glass containers. Since an automatic analyzer often employs a commercially available plastic container, in clinical measurement of cystatin C, it is believed important to prevent a decrease in the measurement accuracy caused by the adsorption of cystatin C to the plastic container. As a method of inhibiting the adsorption of cystatin C to the container, it is thought to subject the container itself to a surface treatment; however, there is a problem in that a surface-treated special container would then be necessary, which results in an increase in the cost.

Therefore, there is a need for a method of accurately and automatically quantifying cystatin C with simple operation, and a means for inhibiting the adsorption of cystatin C to a container in a simple manner is demanded.

PRIOR ART DOCUMENTS

Patent Documents

[Patent Document 1] Japanese Unexamined Patent Application Publication No. 2000-193662
[Patent Document 2] Japanese Patent No. 03342819
[Patent Document 3] Japanese Patent No. 03398372
[Patent Document 4] Japanese Unexamined Patent Application Publication No. 2003-149244

Non-Patent Documents

[Non-patent Document 1] Saito, K. "The 13th Annual Meeting of The Society of Analytical Bio-Science; Measurement of Cystatin C and Its Significance in Clinical Studies", [online], Mar. 14, 2003, [searched on Feb. 8, 2008], Internet

SUMMARY OF THE INVENTION

Problems to be Solved by the Invention

An object of the present invention is to provide a means for inhibiting the adsorption of cystatin C to a container in a simple manner, thereby improving the accuracy of the measurement of cystatin C.

Means for Solving the Problems

The present inventors intensively studied to discover that a non-ionic surfactant has an effect to inhibit the adsorption of cystatin C to a plastic container, thereby completing the present invention.

That is, the present invention provides a cystatin C adsorption inhibitor comprising a non-ionic surfactant. In addition, the present invention provides a cystatin C measurement reagent comprising the aforementioned cystatin C adsorption inhibitor according to the present invention. Further, the present invention provides a cystatin C measurement kit comprising the aforementioned cystatin C adsorption inhibitor according to the present invention. Still further, the present invention provides a method of inhibiting the adsorption of cystatin C, the method comprising bringing a cystatin C-containing sample into contact with a measurement instrument in the presence of a non-ionic surfactant. Yet still further, the present invention provides a method of measuring cystatin C in a sample, the method comprising the step of inhibiting the adsorption of cystatin C to the aforementioned measurement instrument by the aforementioned method of inhibiting the adsorption according to the present invention.

Effects of the Invention

According to the present invention, by a simple method of allowing a non-ionic surfactant to coexist in the measurement system, the adsorption of cystatin C to a measurement instrument such as plastic container can be effectively inhibited. In a clinical test where a large number of specimens are handled at the same time, the measurements of the test samples are usually carried out by an automatic measurement system which employs a plastic measurement container. According to the present invention, accurate measurement values can be attained with simple operation also when measuring cystatin C by such an automatic measurement system; hence, the present invention is very useful in clinical applications.

Mode for Carrying out the Invention

The term "cystatin C adsorption inhibitor" refers to an agent which inhibits the adsorption of cystatin C in a solution to a measurement instrument. Particularly, the adsorption inhibitor can be suitably employed to inhibit the adsorption to a plastic instrument. Here, the term "measurement instrument" used herein refers to a variety of instruments used in a series of operations performed to measure cystatin C, and the term also encompasses, for example, those members contacting the test sample contained in an automatic analyzer. Specific examples of such members include, but are not limited to, plates, containers such as cells, pipettes, and pipette tips. Further, in the present invention, the term "plastic instrument" encompasses not only those instruments that are entirely made of plastic, but also those instruments whose only the surface contacting cystatin C-containing sample is/are made of plastic. For example, the term "plastic container" widely encompasses those containers whose at least the inner wall is made of plastic. The term "plastic" is not particularly restricted and means those synthetic resins that are conventionally used in laboratory instruments, such as polypropylene and polystyrene.

Examples of the non-ionic surfactant used in the present invention include, but are not limited to, secondary alcohol ethoxylates; polyoxyethylene-type non-ionic surfactants such as polyoxyethylene cumylphenylether, p-isooctyl polyoxyethylene phenol-formaldehyde polymer, polyoxyethylene alkylether, polyoxyethylene polycyclic phenylether, polyoxyethylene alkyl propylene diamine, nonylphenol ethoxylate, octylphenylether, polyoxyethylene octylphenylether, polyoxyethylene derivatives, polyoxyethylene sorbitan monooleate, polyoxyethylene-oxypropylene block polymer, lauryl alcohol alkoxylate, polyoxyethylene laurylether, polyoxyethylene monooleate, polyoxyethylene sorbitan monolaurate, polyoxyethylene distyrenated phenylether, polyoxyethylene sorbitan monostearate, polyoxyethylene sorbitan monopalmitate, polyoxyethylene octadecylamine, polyoxyethylene stearylether, polyoxyethylene nonylphenylether, polyoxyethylene oleylether, polyglycerin fatty acid ester, polyoxyethylene benzylphenylether and polyoxyethylene tribenzylphenylether; phosphate ester-type non-ionic surfactants such as aliphatic phosphate esters; and amide-type non-ionic surfactants such as alkylalkylolamide. Further, the non-ionic surfactant may also be used individually or two or more thereof may be used in combination. As concretely shown in Examples below, the amount of the adsorption of cystatin C to a plastic instrument can be reduced by adding such non-ionic surfactant(s) to a cystatin C-containing sample. Such an effect cannot be attained with an ionic surfactant (see Comparative Examples).

Among the non-ionic surfactants, polyoxyethylene-type surfactants are more preferred since the amount of the adsorption of cystatin C in a sample to the container wall becomes particularly small. In addition, non-ionic surfactants having a phenoxy structure as lipophilic group are also preferred. The most preferred thereamong as the non-ionic surfactant used in the present invention is a non-ionic surfactant having a benzylphenoxy structure as lipophilic group, such as polyoxyethylene benzylphenylether or polyoxyethylene tribenzylphenylether. Here, the benzylphenoxy structure is a Ph-$CH_2$-Ph-O-structure, wherein the Ph represents a phenyl group and a part of the hydrogen atoms, H, in the phenyl group or the $CH_2$ group may optionally be substituted by a substituent such as a halogen or an alkyl group.

The HLB value (Hydrophile-Lipophile Balance value) of the non-ionic surfactant is preferably 11 to 16, and particularly more preferably 12.5 to 15. When the HLB value is in this range, the effect to inhibit the adsorption of cystatin C to the measurement instrument is high.

When a surfactant having a benzylphenoxy structure is employed, although the mechanism which enables particularly effective inhibition of the cystatin C adsorption is not certain, it is believed that the benzylphenoxy structure moiety in the linear lipophilic group entwines with the lipophilic moiety of cystatin C or the measurement instrument to inhibit the adsorption of cystatin C to the measurement instrument.

The cystatin C adsorption inhibitor according to the present invention may consist of only a non-ionic surfactant(s), or it may also be in the form of a solution obtained by dissolving a non-ionic surfactant(s) into a buffer. The buffer is not particularly restricted, and any buffer may be employed as long as it does not adversely affect the cystatin C measurement system. As such a buffer, for example, Good buffers, Tris buffers, phosphate-based buffers, carbonate-based buffers, acetate-based buffers and glycine buffers may be employed. As the Good buffer, MES, Bis-Tris, ADA, Bis-Tris propane, PIPES, ACES, cholamine chloride, BES, MOPS, TES, HEPES, HEPPS, Tricine, glycinamide, Bicine, TAPS, CBES, CAPS or the like is suitably employed. Further, the cystatin C adsorption inhibitor may also comprise a known additive such as a stabilizing agent or a chelating agent. Specific examples of the additive include, but are not limited to, stabilizing agents such as bovine serum albumin and casein and chelating agents such as EDTA.

The cystatin C adsorption inhibitor according to the present invention may be used by adding to a cystatin C-containing solution. Examples of the cystatin C-containing solution include those test samples separated from a living body and cystatin C standard solutions used to prepare a calibration curve required for quantifying cystatin C. Examples of the sample separated from a living body include blood, blood serum, blood plasma, urine, stool, saliva, tissue fluid, spinal fluid and swabs, as well as dilutions thereof. The amount of the cystatin C adsorption inhibitor to be used may be appropriately selected in accordance with the amount of cystatin C contained in the solution. The content of the cystatin C adsorption inhibitor in such sample originated from a living body is usually in the range of approximately 0.01 to 100 mg/L, and a calibration curve is also usually prepared using a cystatin C standard solution having this concentration range. Therefore, the amount of the cystatin C adsorption inhibitor to be used is preferably an amount suitable for the cystatin C concentration of 0.01 to 100 mg/L, and specifically, it is preferably 0.001 to 10 w/v %, more preferably 0.01 to 5 w/v %, in terms of the final concentration of the non-ionic surfactant (in terms of the total concentration when a plurality of surfactants are employed).

Such a sample to which the cystatin C adsorption inhibitor is added can be suitably used in any of the known cystatin C measurement methods. Since the adsorption of cystatin C in a sample to an instrument such as plastic container can be effectively inhibited by adding the cystatin C adsorption inhibitor according to the present invention to the sample, it becomes possible to accurately measure cystatin C in the sample.

As the method of measuring cystatin C, immunoassays in which an antibody against cystatin C is used are known (for example, see Patent Documents 1 to 4 and Non-patent Document 1). Cystatin C is a known protein and the antibody thereagainst is also already known. Further, since immunoassays per se are well-known conventional methods, reagents and kits used therefor are also commercially available. The cystatin C adsorption inhibitor according to the present invention may be provided in combination with such commercially available measurement reagent and/or kit. That is, the present invention also provides a measurement reagent and kit comprising the cystatin C adsorption inhibitor. Here, in addition to sample dilutions, antibody dilutions, washing solutions, enzyme solutions, substrate solutions and the like, the term "measurement reagent" used herein also encompasses the aforementioned cystatin C standard solution. Since an addition of the cystatin C adsorption inhibitor according to the present invention to the cystatin C standard solution allows measurements of cystatin C in the standard solution, an accurate calibration curve can be prepared.

As described in the above, by utilizing the cystatin C adsorption inhibitor comprising a non-ionic surfactant(s), the adsorption of cystatin C in a sample such as a biological sample to the measurement instrument can be inhibited. That is, the present invention also provides a method of inhibiting the adsorption of cystatin C, the method comprising bringing a cystatin C-containing sample into contact with a measurement instrument in the presence of a non-ionic surfactant. The term "method of inhibiting the adsorption" used herein refers to inhibiting the adsorption of cystatin C in a sample to a measurement instrument such as plastic container. The conditions of the non-ionic surfactant(s), the concentration thereof and the cystatin C-containing sample, which are used in the method of inhibiting the adsorption, are the same as those described in the above regarding the adsorption inhibitor.

Further, the present invention also provides a method of measuring cystatin C in a sample, the method comprising the step of inhibiting the adsorption of cystatin C to a measurement instrument by the aforementioned method of inhibiting the adsorption of cystatin C. The measurement method is preferably carried out by immunoassay. By employing the aforementioned method of inhibiting the adsorption, the accuracy of the measurement of cystatin C can be improved, so that cystatin C in the sample can be accurately measured. It is preferred that the step of performing the method of inhibiting the adsorption be done before bringing the sample into contact with the measurement container such as measurement plate. For example, it is preferred that the sample and non-ionic surfactant(s) be mixed in the step of preparing a sample to be measured. It is noted here that, in the present invention, the term "measurement" includes "detection", "quantification" and "semi-quantification".

The measurement per se of cystatin C in the sample may employ any known method. For example, immunoassays using an antibody against cystatin C are known (for example, see Patent Documents 1 to 4 and Non-patent Document 1), and such a known method may be employed. However, since immunoassays per se are well-known as described in the above, the method of measuring cystatin C is not restricted to those known methods and any immunoassay may also be applied. That is, when classifying on the basis of the reaction type, known immunoassays include sandwich methods, competition methods, agglutination methods, immunochromatography methods and the like, and when classifying on the basis of the label employed, known immunoassays include enzyme immunoassays, radio immunoassays, fluorescence immunoassays, chemiluminescence immunoassays and the like. Any of these are included in the term "immunoassay" used in the present invention and may be employed as the aforementioned immunoassay. Further, as described in the above, cystatin C is a known a protein and the anti-cystatin C antibody is also known. These can be easily obtained as there are also commercially available products thereof. Moreover, methods of preparing a known protein by a genetic engineering technique, as well as methods of preparing antibodies against a known protein, such as polyclonal antibodies and monoclonal antibodies, and antigen-binding fragments (antibody fragments, such as Fab fragments and (ab')$_2$ fragments, which retain a property to bind with the corresponding antigens), are also well-known conventional methods in the art; therefore, one of ordinary skill in the art would be able to easily prepare an antibody against cystatin C or its antigen-binding fragment.

As the sample used in the method of measuring cystatin C according to the present invention, a sample separated from a living body is preferred, and examples thereof include blood, blood serum, blood plasma, urine, stool, saliva, tissue fluid, spinal fluid and swabs, as well as dilutions thereof. In the measurement method according to the present invention, particularly, a body fluid of a blood origin, such as blood, blood serum or blood plasma, as well as a dilution thereof, is suitably used.

In Examples described below, an immunoagglutination method is employed. The immunoagglutination method will now be explained; however, the explanation is not intended to restrict the scope of the present invention to the immunoagglutination method.

An immunoagglutination method is a method of detecting or quantifying an antigen or antibody in a test sample based on a change in an optical property such as turbidity or absorbance of the reaction solution, which change is caused by antigen-antibody reaction. Immunoagglutination method includes turbidimetric immunoassay and immunonephelometry. In an immunoagglutination method, sensitized particles, for example, colloidal gold or latex particles are used. In an immunoagglutination method, the test substance (cystatin C in the present invention) is measured on the basis of a change in an optical property such as turbidity or absorbance of the solution, which change is caused by antigen-antibody reaction between an antigen in the sample and an antibody of the sensitized particles or between an antibody in the sample and an antigen of the sensitized particles. Immunoagglutination methods in which latex particles are used are also referred to as latex agglutination method. Some of the immunoagglutination methods employ antiserum in place of sensitized particles.

In cases where immunoagglutination method is employed as the method of measuring cystatin C according to the present invention, the concentration of the sensitized particles in the reaction solution is usually about 0.01 to 0.5%, and the reaction is performed usually at a temperature of 1 to 55° C., preferably 35 to 40° C., for about 1 to 10 minutes. The reaction medium is not particularly restricted, and various buffers such as glycine buffers and Good's buffers may be employed.

The concentration of cystatin C in the sample is calculated based on the amount of change (end-point method) or on the rate of the change (rate method) in the measured turbidity or absorbance of the reaction solution. The end-point method is based on the amount of change in the turbidity or absorbance measured before the reaction and at a prescribed time after the reaction, and the rate method is based on the amount of change in the turbidity or absorbance measured before the reaction and after the reaction with time. The immunoagglutination method may be carried out manually or by using a known automatic analyzer.

EXAMPLES

The present invention will now be described more concretely by way of examples thereof. However, the present invention is not restricted to the following examples.

(Preparation of Sample Solutions)

To 50 mM Hepes buffer (pH 7.5), each of the surfactants listed below was added in an amount of 0.1 (w/v) % to prepare base solutions. Cystatin C antigen was added to each of the thus prepared base solutions to a concentration of approximately 1 mg/L to prepare sample solutions.

The thus prepared samples solutions were transferred to two brand-new Hitachi automatic analyzer sample cups, and one of them was designated "Sample without transfer". The other sample was transferred to a new sample cup and sufficiently allowed to contact with the cup by adequately stirring with vortex. This operation was repeated once more to perform a total of two transfers. The thus obtained sample solution was designated "Sample with two transfers". Further, as Comparative Examples, sample solutions comprising no surfactant in the base solution were prepared and subjected to measurement of the change in absorbance in the same manner as Examples.

(Materials used)

Non-ionic surfactant A: EMULGEN 707 non-ionic surfactant (manufactured by Kao Corporation; the main component is polyoxyethylene alkylether); HLB value=12.1

Non-ionic surfactant B: EMULGEN A-90 non-ionic surfactant (manufactured by Kao Corporation; the main component is polyoxyethylene distyrenated phenylether); HLB value=14.5

Non-ionic surfactant C: EMULGEN B-66 non-ionic surfactant (manufactured by Kao Corporation; the main component is polyoxyethylene tribenzylphenylether); HLB value =13.2

Non-ionic surfactant D: TWEEN 80 non-ionic surfactant (manufactured by Sigma; the main component is polyoxyethylene sorbitan monooleate); HLB value =15.0

Anionic surfactant A: PS-1 anionic surfactant (manufactured by Tosoh Corporation; the main component is sodium polystyrene sulfonate)

Anionic surfactant B: PELEX NBL anionic surfactant (manufactured by Kao Corporation; the main component is sodium alkyl naphthalene sulfonate)

Cystatin C antigen: recombinant human cystatin C (manufactured by DAKO)

reaction was measured during a period of about 5 minutes in terms of the amount of the change in absorbance at 546 nm to compare the cystatin C concentrations. Samples having known concentrations were subjected to the measurement under the same conditions to prepare a calibration curve based on the relationship between the concentration of cystatin C and the amount of the change in absorbance. An accessory software of the automatic analyzer was used to measure the change in absorbance, prepare the calibration curve and calculate the quantitative values.

The adsorption rate was calculated using the following equation, and the adsorption-inhibiting ability of cystatin C was evaluated in each test material in accordance with the following assessment criteria.

Adsorption Rate [%]=Cystatin C Concentration in Sample Solution with Two Transfers/(Cystatin C Concentration in Sample Solution without Transfer−1)×100

Assessment Criteria:

⊚ (Excellent): The absolute value of the adsorption rate is not greater than 1%.

○ (Good): The absolute value of the adsorption rate is not greater than 10%.

x (Not acceptable): The absolute value of the adsorption rate is greater than 10%.

TABLE 1

| | Type of Surfactant | Main Component of Surfactant (Final concentration of the surfactant is indicated in parentheses) | Cystatin C Concentration before and after Transfer (mg/L) | | Adsorption Rate of Cystatin C before and after Transfer (%) (B/A − 1) × 100 | Assessment |
| --- | --- | --- | --- | --- | --- | --- |
| | | | No transfer A | Two transfers B | | |
| Comparative Example 1 | — | Hepes buffer (50 mM) | 0.935 | 0.695 | −25.7 | X |
| Example 1 | Non-ionic surfactant A | Polyoxyethylene alkylether (0.1%) | 0.998 | 1.015 | 1.7 | ○ |
| Example 2 | Non-ionic surfactant B | Polyoxyethylene distyrenated phenylether (0.1%) | 0.943 | 0.950 | 0.7 | ⊚ |
| Example 3 | Non-ionic surfactant C | Polyoxyethylene tribenzylphenylether (0.1%) | 0.954 | 0.954 | 0.0 | ⊚ |
| Example 4 | Non-ionic surfactant D | Polyoxyethylene sorbitan monooleate (0.1%) | 0.953 | 0.936 | −1.8 | ○ |
| Comparative Example 2 | Anionic surfactant A | Sodium polystyrene sulfonate (0.1%) | 0.898 | 0.703 | −21.7 | X |
| Comparative Example 3 | Anionic surfactant B | Sodium alkyl naphthalene sulfonate (0.1%) | 0.695 | 0.444 | −36.1 | X |

Note 1:
A smaller absolute value of the adsorption rate means a smaller amount of adsorption.

(Measurement reagents)

First reagent: comprises 100 mM Tris buffer (pH 8.5) and 500 mM sodium chloride

Second reagent: anti-human cystatin C antibody-sensitized latex suspension

Measurement method: Automatic measurement was carried out by end-point method using Hitachi 7180 Automatic Clinical Analyzer (manufactured by Hitachi Ltd).

(Measurement by Automatic Analyzer)

The concentration of cystatin C in each sample was measured by using the aforementioned cystatin C measurement reagents. Added to 3 μL of the above-prepared sample solution was 230 μL of the first reagent, and the resulting mixture was stirred at 37° C. and left to stand for 5 minutes. Thereafter, 50 μL of the second reagent was added and the resulting mixture was further stirred at 37±0.1° C. The agglutination (Discussion)

The adsorption of cystatin C to the sample cup was simply inhibited by using the non-ionic surfactants. By this, it was shown that cystatin C can be accurately quantified with simple operation by using the automatic analyzer.

The invention claimed is:

1. A method of improving the measurement of cystatin C in a sample, said method comprising:
   inhibiting the adsorption of cystatin C to a measurement instrument comprising bringing a cystatin C-containing sample into contact with the measurement instrument in the presence of a non-ionic surfactant, wherein said non-ionic surfactant is selected from the group consisting of polyoxyethylene distyrenated phenylether, and polyoxyethylene tribenzylphenylether and
   measuring the amount of cystatin C in the sample.

2. The method of measuring according to claim 1, wherein said non-ionic surfactant is present in an amount of 0.001 to 10 w/v %.

3. The method of measuring according to claim 2, wherein said non-ionic surfactant is present in an amount of 0.01 to 5 w/v %.

4. The method of measuring according to claim 1, wherein said measurement instrument is a plastic container.

5. The method of measuring according to claim 1, wherein said method is carried out by an immunoassay.

* * * * *